(12) United States Patent
Harrington

(10) Patent No.: US 11,395,884 B2
(45) Date of Patent: Jul. 26, 2022

(54) MECHANISM FOR REDUCING RISK OF DRUG CONTAMINATION

(71) Applicant: Novo Nordisk A/S, Bagsvaerd (DK)

(72) Inventor: Roger Harrington, Skaevinge (DK)

(73) Assignee: Novo Nordisk A/S, Bagsvaerd (DK)

( * ) Notice: Subject to any disclaimer, the term of this patent is extended or adjusted under 35 U.S.C. 154(b) by 1059 days.

(21) Appl. No.: 16/065,278

(22) PCT Filed: Dec. 29, 2016

(86) PCT No.: PCT/EP2016/082834
§ 371 (c)(1),
(2) Date: Jun. 22, 2018

(87) PCT Pub. No.: WO2017/114894
PCT Pub. Date: Jul. 6, 2017

(65) Prior Publication Data
US 2021/0069427 A1    Mar. 11, 2021

(30) Foreign Application Priority Data
Dec. 30, 2015   (EP) .................................... 15203094

(51) Int. Cl.
*A61M 5/32* (2006.01)
*A61M 5/24* (2006.01)
*A61M 5/34* (2006.01)

(52) U.S. Cl.
CPC ............ *A61M 5/3202* (2013.01); *A61M 5/24* (2013.01); *A61M 5/3245* (2013.01); *A61M 5/347* (2013.01); *A61M 2005/2488* (2013.01)

(58) Field of Classification Search
CPC .... A61M 5/3202; A61M 5/24; A61M 5/3245; A61M 5/347; A61M 2005/2488;
(Continued)

(56) References Cited

U.S. PATENT DOCUMENTS 4,921,491 A   5/1990   Champ
7,540,858 B2  6/2009   DiBiasi
(Continued)

FOREIGN PATENT DOCUMENTS

CN   102844065     12/2012
CN   103108666 A    5/2013
(Continued)

*Primary Examiner* — James D Ponton
*Assistant Examiner* — Neeraja Gollamudi
(74) *Attorney, Agent, or Firm* — Wesley Nicolas

(57) ABSTRACT

The present invention provides a drug delivery system (1) comprising a drug delivery device (2, 3) carrying at least one reservoir (40a, 40b), and a needle unit (4) being attachable to the drug delivery device (2, 3) in axial extension thereof and adapted to establish a flow way between the at least one reservoir (40a, 40b) and a drug delivery site. The needle unit (4) comprises a needle structure (11) comprising a front needle portion (12) for entering the drug delivery site, and at least one back needle portion (13a, 13b) for insertion into the at least one reservoir (40a, 40b), and a needle shield (20). The needle shield (20) and the needle structure (11) are capable of undergoing relative axial motion between an accommodating relative position in which the needle structure (11) is completely accommodated within the needle shield (20) and a protruding relative position in which the front needle portion (12) protrudes from the needle shield (20), the needle shield (20) and the needle structure (11) being biased towards the accommodating relative position by a first bias force. When the needle unit (4) is attached to the drug delivery device (2, 3) the needle structure (11) and the at least one reservoir (40a, 40b) are capable of undergoing relative axial motion between a disconnected relative position in which the at least one back needle portion (13a, 13b) is spaced apart from the at least one reservoir (40a, 40b), and a connected relative position in which the at least one back needle portion (13a, 13b) and the at least one (Continued)

reservoir (40a, 40b) are fluidly connected, the needle structure (11) and the at least one reservoir (40a, 40b) being biased towards the disconnected relative position by a second bias force which is greater than the first bias force.

5 Claims, 11 Drawing Sheets

(58) Field of Classification Search
CPC .. A61M 2005/2474; A61M 2005/3267; A61M 5/3219; A61M 5/3232; A61M 5/3234; A61M 5/3257; A61M 5/326; A61M 5/3271; A61M 5/3275; A61M 5/3298; A61M 5/2066; A61M 5/2448; A61M 5/2455; A61M 5/285
See application file for complete search history.

(56) References Cited

U.S. PATENT DOCUMENTS

| | | | |
|---|---|---|---|
| 9,033,933 B2 | 5/2015 | Boyd et al. | |
| 9,180,277 B2 | 11/2015 | Erskine | |
| 9,233,209 B2 | 1/2016 | Markussen et al. | |
| 9,616,183 B2 | 4/2017 | Wozencroft | |
| 9,789,264 B2 | 10/2017 | Roberts et al. | |
| 9,833,579 B2 | 12/2017 | Pedersen et al. | |
| 10,117,994 B2 | 11/2018 | Holtwick et al. | |
| 10,159,803 B2 | 12/2018 | Dasbach | |
| 2003/0078546 A1 | 4/2003 | Jensen | |
| 2015/0065917 A1 | 3/2015 | Ierfino | |
| 2015/0080810 A1 | 3/2015 | Henderson et al. | |
| 2015/0157797 A1* | 6/2015 | Eggert | A61M 5/3298 604/506 |
| 2015/0273161 A1* | 10/2015 | Bengtsson | A61M 5/326 604/198 |

FOREIGN PATENT DOCUMENTS

| | | | |
|---|---|---|---|
| CN | 103118723 A | 5/2013 | |
| CN | 103167887 A | 6/2013 | |
| CN | 103282065 A | 9/2013 | |
| CN | 103354754 A | 10/2013 | |
| CN | 104379195 A | 2/2015 | |
| CN | 104968385 A | 10/2015 | |
| EP | 2853277 A1 | 4/2015 | |
| JP | 2008246190 A | 10/2008 | |
| JP | 2014518662 A | 8/2014 | |
| JP | 2015532191 A | 11/2015 | |
| WO | WO-2014064100 A1 * | 5/2014 | A61M 5/3286 |

* cited by examiner

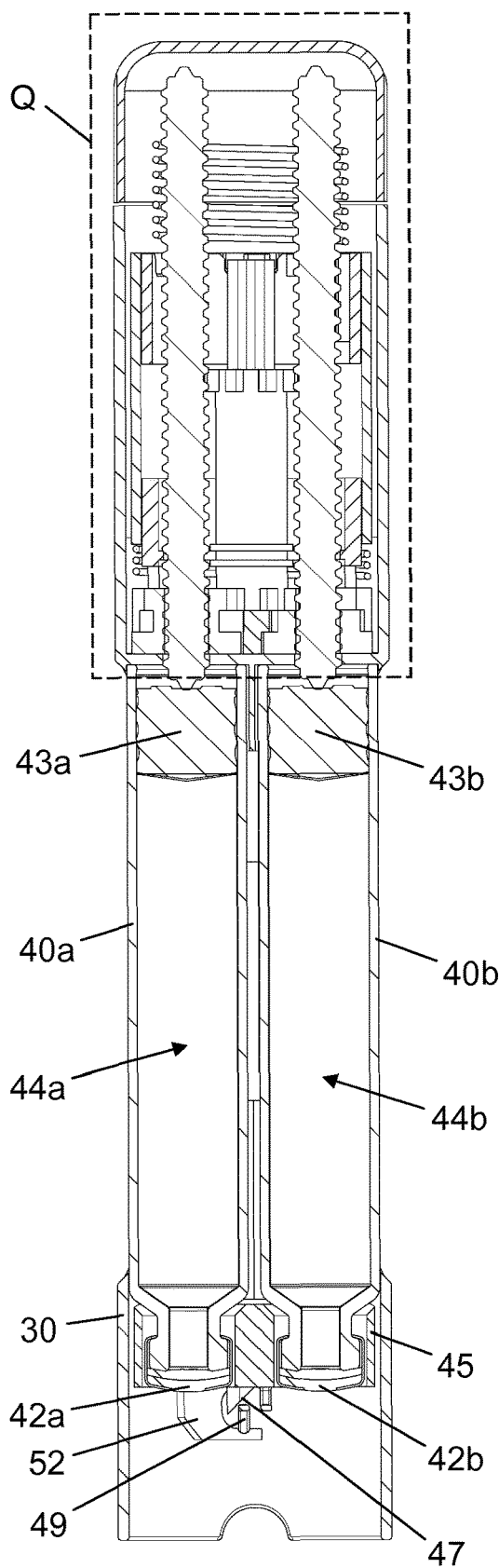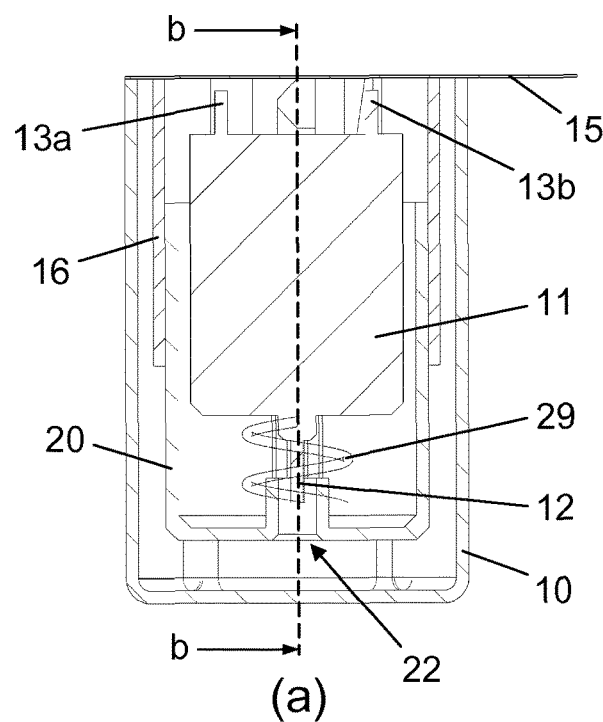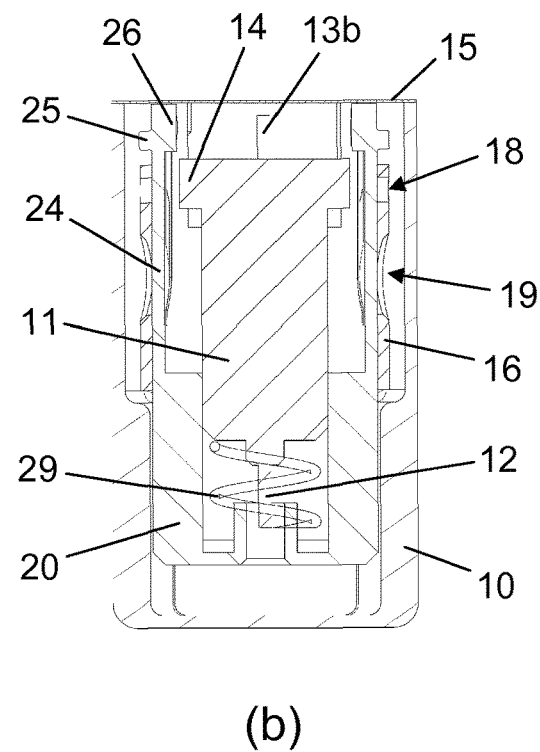
Fig. 2
Fig. 3

MECHANISM FOR REDUCING RISK OF DRUG CONTAMINATION

CROSS-REFERENCE TO RELATED APPLICATIONS

This application is a 35 U.S.C. § 371 National Stage application of International Application PCT/EP2016/082834 (published as WO 2017/114894), filed Dec.29, 2016, which claims priority to European Patent Application 15203094.6, filed De. 30, 2015, the contents thereof which are incorporated by reference in their entirety.

FIELD OF THE INVENTION

The present invention relates to drug delivery devices and particularly to injection devices for use with replaceable injection needle assemblies.

BACKGROUND OF THE INVENTION

Many drugs must be administered parenterally to be effective in the body and some of these, e.g. insulin and glp-1, may require one or more doses to be delivered subcutaneously on a daily basis. Subcutaneous drug delivery is often associated with discomfort as many people dislike the thought of having an injection needle inserted through the skin. An undisclosed number of people even suffer from needle-phobia, and these people often benefit from using needle assemblies with shielded needles, where the injection needle remains out of sight during handling of the needle assembly, including insertion of the injection needle into the skin.

Typically, this type of needle assembly comprises an axially movable sheath which can be slid between a first position in which it covers the injection needle and a second position in which the injection needle is exposed and ready for injection. In some cases the sheath is spring loaded such that it is automatically slid to the first position when the injection needle is retracted from the skin. An example of this is disclosed in US 2003/0078546.

A conventional needle assembly comprises a front needle configured for insertion into the skin and one or two back needles being fluidly connected with the front needle and being configured for easy entry into, respectively, one or two substance reservoirs. However, as long as a flow line is open between the body and a substance reservoir there is a risk of body fluids entering the reservoir interior and contaminating the contents thereof. This is particularly undesired if the substance reservoir is to be used over time for more than one injection.

SUMMARY OF THE INVENTION

It is an object of the invention to eliminate or reduce at least one drawback of the prior art, or to provide a useful alternative to prior art solutions.

In particular, it is an object of the invention to provide a drug delivery system which offers a reduced risk of drug contamination.

In the disclosure of the present invention, aspects and embodiments will be described which will address one or more of the above objects and/or which will address objects apparent from the following text.

In one aspect of the invention a drug delivery system is provided, comprising: A) a drug delivery device carrying at least one reservoir, and B) a needle unit being attachable to the drug delivery device in axial extension thereof and adapted to establish a flow way between the at least one reservoir and a drug delivery site, the needle unit comprising b1) a needle structure comprising a front needle portion for entering the drug delivery site, and at least one back needle portion for insertion into the at least one reservoir, and b2) a needle shield, wherein the needle shield and the needle structure are capable of undergoing relative axial motion between an accommodating relative position in which the needle structure is completely accommodated within the needle shield, and a protruding relative position in which the front needle portion protrudes from the needle shield, the needle shield and the needle structure being biased towards the accommodating relative position by a first bias force, wherein when the needle unit is attached to the drug delivery device the needle structure and the at least one reservoir are capable of undergoing relative axial motion between a disconnected relative position in which the at least one back needle portion is spaced apart from the at least one reservoir, and a connected relative position in which the at least one back needle portion and the at least one reservoir are fluidly connected, the needle structure and the at least one reservoir being biased towards the disconnected relative position by a second bias force, and wherein the second bias force is greater than the first bias force, such that when an axial compressive force presses the needle unit and the drug delivery device together the needle shield and the needle structure reach the protruding relative position before the needle structure and the at least one reservoir reach the connected relative position, and when the compressive force is discontinued the needle shield and the needle structure reach the accommodating relative position after the needle structure and the at least one reservoir reach the disconnected relative position.

The inventor has established that in order to minimise the risk of drug contamination it is important that a fluid communication with any present reservoir be established after insertion of the front needle in the skin and interrupted before withdrawal of the front needle from the skin. The above described drug delivery system comprises an integrated mechanism which ensures that both the establishment and the interruption of the flow ways occur properly according to this desired sequence.

The first bias force may be provided by a first spring member arranged to act between the needle shield and a distally directed surface of the needle structure, and the second bias force may be provided by a second spring member arranged on a distal end surface of the drug delivery device. Other means for providing the respective bias forces may alternatively be employed, such as e.g. suitable foam structures.

The arrangement of the second spring member on the drug delivery device ensures that its use follows the lifetime of the drug delivery device. This reduces the number of single use components and hence the waste connected with the disposable needle unit.

The at least one reservoir may comprise a first cartridge having a first penetrable septum and a second cartridge having a second penetrable septum. Furthermore, the at least one back needle portion may comprise a first back needle portion and a second back needle portion, and each of the first back needle portion and the second back needle portion may be fluidly connected with the front needle portion, e.g. in a needle manifold configuration.

The first back needle portion may be adapted to penetrate the first penetrable septum to establish a first flow way between the first cartridge and the front needle portion, and the second back needle portion may be adapted to penetrate the second penetrable septum to establish a second flow way between the second cartridge and the front needle portion. This provides for delivery of a volume of a first content of the first cartridge and a volume of a second content of the second cartridge through a single skin inserted needle, reducing the number of skin penetrations needed for a subcutaneous treatment involving simultaneous or sequential delivery of more than one individual substance.

The needle shield may comprise a longitudinally extending arm carrying a protrusion, and the drug delivery device may comprise a retaining hook adapted to interact with the protrusion to secure the needle unit on the drug delivery device.

In a pre-connected state of the needle structure the longitudinally extending arm may be radially deflectable relative to a remaining portion of the needle shield from a non-deflected position in which the retaining hook is capable of interacting with the protrusion to a radially deflected position in which the retaining hook is incapable of interacting with the protrusion. For example, the longitudinally extending arm may be a cantilever, and the protrusion may be arranged at or near the free end portion of the cantilever. The longitudinally extending arm may be biased towards the non-deflected position.

Thereby, the longitudinally extending arm may be manipulated to allow the protrusion to pass the retaining hook, either to attach the needle unit to the drug delivery device or to detach the needle unit from the drug delivery device. By pressing the longitudinally extending arm radially inwardly the protrusion is moved out of the plane of the retaining hook, allowing longitudinal relative motion between the needle shield and the retaining hook. The bias of the longitudinally extending arm moves the protrusion back to the plane of the retaining hook upon a discontinuation of the manipulation.

The needle unit may further comprise a needle housing surrounding respective portions of the needle structure and the needle shield. The needle housing may comprise a cylindrical wall having an opening therein, and the opening may be aligned with the longitudinally extending arm, allowing a user to apply a radial force to the longitudinally extending arm through the opening.

The opening in the needle housing thus allows a user to move the protrusion out of the plane of the retaining hook by using a fingertip to press the longitudinally extending arm radially inwardly. The longitudinally extending arm is hence manipulable even with the presence of the needle housing.

The longitudinally extending arm may also be laterally deflectable relative to the remaining portion of the needle shield from the non-deflected position to a laterally deflected position, against a lateral bias force biasing the longitudinally extending arm towards the non-deflected position, and the needle housing may further comprise a bayonet track adapted to receive and retain the protrusion. Further, the longitudinally extending arm may comprise a first ramp surface and the drug delivery device may comprise a second ramp surface, which first ramp surface and second ramp surface are arranged to slide along one another during relative axial motion of the needle structure and the at least one reservoir from the connected relative position to the disconnected relative position, thereby causing the longitudinally extending arm to move from the non-deflected position to the laterally deflected position and back to the non-deflected position, guiding the protrusion from the retaining hook to an end portion of the bayonet track.

The needle shield and the needle structure may further be configured to undergo a final relative axial motion from the accommodating relative position to a post-use accommodating relative position in response to the relative axial motion of the needle structure and the at least one reservoir from the connected relative position to the disconnected relative position, and the needle structure may further comprise a radial protuberance which is moved into radial alignment with the protrusion during the final relative axial motion between the needle shield and the needle structure.

The radial alignment of the radial protuberance and the protrusion in the post-use accommodating relative position of the needle shield and the needle structure prevents radial deflection of the portion of the longitudinally extending arm which carries the protrusion, thereby preventing the protrusion from leaving the bayonet track. The inescapable position of the protrusion at the end portion of the bayonet track effectively locks the needle shield and the needle housing axially, whereby it is ensured that the needle unit cannot be reused, further reducing the risk of contamination and/or cross-contamination of the reservoir contents.

In the present specification, reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in, or inherent of, at least that one aspect or embodiment of the invention, but not necessarily in/of all aspects or embodiments of the invention. It is emphasized, however, that any combination of the various features, structures and/or characteristics described in relation to the invention is encompassed by the invention unless expressly stated herein or clearly contradicted by context.

The use of any and all examples, or exemplary language (e.g., such as, etc.), in the text is intended to merely illuminate the invention and does not pose a limitation on the scope of the same, unless otherwise claimed. Further, no language or wording in the specification should be construed as indicating any non-claimed element as essential to the practice of the invention.

BRIEF DESCRIPTION OF THE DRAWINGS

In the following the invention will be further described with references to the drawings, wherein FIG. 2 is a longitudinal section view of a drug delivery device forming part of the drug delivery system, FIG. 3 shows two longitudinal section views of a needle module for use with the drug delivery device.

In the figures like structures are mainly identified by like reference numerals.

DESCRIPTION OF EXEMPLARY EMBODIMENTS

When in the following relative expressions, such as "upper" and "lower", are used, these refer to the appended figures and not necessarily to an actual situation of use. The shown figures are schematic representations for which reason the configuration of the different structures as well as their relative dimensions are intended to serve illustrative purposes only.

Figure 1:
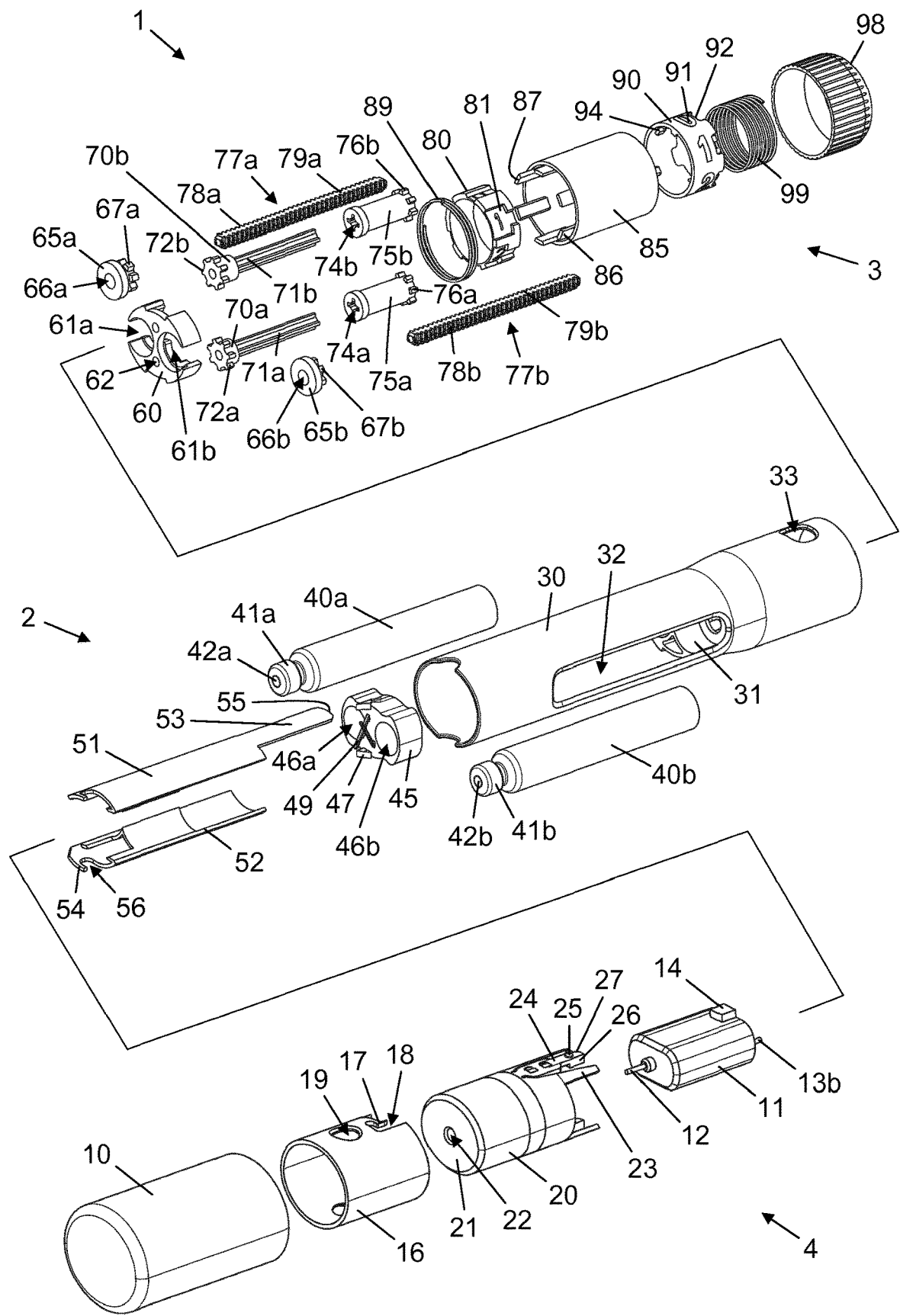
FIG. 1 is an exploded view of a drug delivery system according to an embodiment of the invention.

FIG. 1 is an exploded view of a drug delivery system 1 according to an exemplary embodiment of the invention. The drug delivery system 1 comprises a drug delivery device 2, 3 to be used with a separate needle module 4. The drug delivery device 2, 3 comprises a device housing structure 2 and a dose engine 3.

The device housing structure 2 comprises a main body 30 adapted to accommodate a first cartridge 40a holding a first substance, a second cartridge 40b holding a second substance, as well as a portion of the dose engine 3. The needle module 4 is a single use unit which is attachable to a distal end portion of the device housing structure 2 and which can be used for effecting one sequential administration of the first substance and the second substance.

The main body 30 extends along a longitudinal axis and is provided with an elongated central window 32 allowing for inspection of the respective cartridge contents, and a small dose window 33 at a proximal end portion for verification of a set dose. Just proximally of the elongated central window 32 a bulkhead 31 separates a cartridge accommodating portion of the main body 30 from a dose engine accommodating portion.

Axially and rotationally fixed within the main body is a cartridge chassis 45, serving to retain the first cartridge 40a and the second cartridge 40b in predefined positions against the bulkhead 31. The cartridge chassis 45 has a first cartridge receiving bore 46a adapted to envelop an outlet end portion 41a of the first cartridge 40a and a second cartridge receiving bore 46a adapted to envelop an outlet end portion 41b of the second cartridge 40b. On a distal end face the cartridge chassis 45 carries a pair of chassis chamfers 47 and a chassis spring 49, the respective purposes of which will be explained below.

A first shield transfer element 51 and a diametrically opposite second shield transfer element 52 extend longitudinally within the main body 30. The first shield transfer element 51 comprises a transfer leg 53 which extends through the bulkhead 31 and into the dose engine accommodating portion, the bulkhead 31 thereby rotationally fixing the first shield transfer element 51 with respect to the main body 30. The transfer leg 53 has a proximally oriented abutment surface 55 for interaction with parts of the dose engine 3, as explained further below. Both shield transfer elements 51, 52 have a distal retaining hook 54, the arrangement of which defining respective receiving spaces 56.

The needle module 4 comprises a needle hub 11 having a front needle 12 for penetration of human skin, a first back needle 13a (not visible) adapted to penetrate a first self-sealing septum 42a closing the outlet end portion 41a of the first cartridge 40a, and a second back needle 13b adapted to penetrate a second self-sealing septum 42b closing the outlet end portion 41b of the first cartridge 40b. Both back needles 13a, 13b are fluidly connected with the front needle 12 such that the first substance may be transferred from the first cartridge 40a through the first back needle 13a and the front needle 12 to a desired, e.g. subcutaneous, delivery site, and the second substance may be transferred from the second cartridge 40b through the second back needle 13b and the front needle 12 to the same delivery site.

The needle hub 11 is slidably received in a needle shield 20 such that in a non-active state of the needle module 4 the front needle 12 is positioned behind an end wall 21, thereby eliminating any risks of accidental needle pricking. However, during use, in an active state of the needle module 4, the front needle 12 protrudes from a bore 22 in the end wall 21. The needle hub 11 is biased proximally, i.e. away from the end wall 21, by a needle return spring 29 (see FIG. 3) in the needle shield 20.

The needle shield 20 has a number of proximally extending legs 23 as well as a pair of diametrically opposite radially and laterally deflectable arms 24. Each arm 24 carries a guide pin 25, a proximal thickened portion 26, and a shield chamfer 27, the latter being adapted for cooperation with a respective one of the chassis chamfers 47 following a finalised dose administration, and the thickened portion 26 being adapted for cooperation with a raised surface 14 on the needle hub 11 when the needle shield 20 and the needle hub 11 are in a certain relative axial position.

A needle housing 16 accommodates a portion of the needle shield 20 and serves to position the needle module 4 properly on the device housing structure 2 as well as to prevent reuse of a used needle module 4. To the effect of the latter the needle housing 16 is provided with a finger 17 at a proximal end portion, the finger 17 defining a bayonet track 18 adapted to receive the guide pin 25 in a manner which will be described further below. A pair of diametrically opposite openings 19 allow for user manipulation of the arms 24 to dismount the needle module 4 from the device housing structure 2. Notably, this is only possible before the front needle 12 is caused to protrude from the bore 22.

Before use of the needle module 4 the needle hub 11, the needle shield 20, and the needle housing 16 are accommodated in an outer cap 10 which is sealed by a removable sterile barrier in the form of a peel-off foil 15 (see FIG. 3).

The dose engine 3 comprises a gear chassis 60 having two holes 62 through which respective stub shafts 36a, 36b (see FIG. 4b) on the proximal side of the bulkhead 31 extend. The gear chassis 60 further has a first bearing 61a for a first piston rod guide 65a and a second bearing 61b for a second piston rod guide 65b. The first piston rod guide 61a has a threaded pass-through 66a and a toothed rim 67a, while the second piston rod guide 61b has a threaded pass-through 66b and a toothed rim 67b. The toothed rims 67a, 67b are axially offset from one another.

A first piston rod 77a having an interrupted thread 78a along its entire length and an axially extending smooth surface 79a is configured for reception in the pass-through 66a. Similarly, a second piston rod 77b having an interrupted thread 78b along its entire length and an axially extending smooth surface 79b is configured for reception in the pass-through 66b. The two piston rods 77a, 77b are thus arranged in parallel, and they extend through respective first and second through holes 35a, 35b (see FIG. 10) in the bulkhead 31. The first through hole 35a has a flattened cross-section to prevent relative rotational motion between the first piston rod 77a and the main body 30. Similarly, the second through hole 35b has a flattened cross-section to prevent relative rotational motion between the second piston rod 77b and the main body 30.

Also arranged in parallel but at right angles to the two piston rods 77a, 77b are a first lay shaft 70a and a second lay shaft 70b. The first lay shaft 70a comprises a cruciform shaft portion 71a, on which a first top gear 75a having a corresponding cruciform bore 74a is slidably mounted, and a toothed rim 72a. The second lay shaft 70b comprises a cruciform shaft portion 71b, on which a first top gear 75b having a corresponding cruciform bore 74b is slidably mounted, and a toothed rim 72b. The toothed rims 72a, 72b are axially offset from one another, such that the toothed rim 72a on the first lay shaft 70a is aligned with the toothed rim 67a on the first piston rod guide 65a and the toothed rim 72b on the second lay shaft 70b is aligned with the toothed rim 67b on the second piston rod guide 65b. Thereby, the first lay shaft 70a is rotationally coupled with the first piston rod guide 65a and the second lay shaft 70b is rotationally coupled with the second piston rod guide 65b.

An axially slidable and rotatable annular dose locator 80 is arranged about the two piston rods 77a, 77b and the two lay shafts 70a, 70b. The dose locator 80 is axially fixed to the two top gears 75a, 75b and is provided with a plurality of differently sized pockets 81 configured to receive the transfer leg 53 of the first shield transfer element 51.

The dose locator 80 is surrounded by a transparent cylindrical scale connector 85 having a plurality of splines 86 which extend distally through respective longitudinal tracks 82 (see FIG. 11a) in the dose locator 80, thereby rotationally fixing the dose locator 80 to the scale connector 85. Each of the splines 86 has an abutment surface 87 for interaction with the abutment surface 55 on the transfer leg 53. The scale connector 85 is translationally and rotationally biased by a dose locator return spring 89, as described further below.

A scale drum 90 carrying a plurality of dose related ciphers 91 is arranged within the scale connector 85, proximally of the dose locator 80. At its proximal rim the scale drum 90 is provided with a plurality of indents 92. In a dose setting state of the drug delivery device 2, 3 the scale drum 90 is rotationally fixed to the scale connector 85 via these indents 92 and mating radial protrusions 88 (see FIG. 4a) on an interior surface of the scale connector 85, and a dose can be set by rotation of a dose dial 98.

A plurality of radially inwardly protruding teeth 94 are provided on the scale drum 90 in a specific pattern which will be explained in detail below. The teeth 94 are arranged to mesh with, respectively, a toothed rim 76a on the first top gear 75a and a toothed rim 76b on the second top gear 75b during a sequential dose administration. The dosing mechanism is powered by a torsion spring 99 in a manner generally known from automatic injection pens used in the diabetes care segment and may be released automatically, e.g. in response to the first shield transfer element 51 reaching a particular axial position in the main body 30, or manually by the user operating a dedicated dose release button (not shown).

FIG. 2 is a longitudinal section view of the drug delivery device 2, 3 before attachment of the needle module 4. It shows the two cartridges 40a, 40b arranged side by side with the respective self-sealing septa 42a, 42b pointing downwards. The first cartridge 40a is sealed at its upper end by an axially slidable piston 43a which together with the first self-sealing septum 42a and the cartridge wall defines a first chamber 44a in which the first substance is contained. Similarly, the second cartridge 40b is sealed at its upper end by an axially slidable piston 43b which together with the second self-sealing septum 42b and the cartridge wall defines a second chamber 44b in which the second substance is contained.

FIG. 3a is a longitudinal section view of the needle module 4 in a pre-use state in which the needle hub 11 is aseptically housed in a sealed space defined by the outer cap 10 and the peel-off foil 15. The needle return spring 29 is a compression spring acting between the needle hub 11 and the needle shield 20.

FIG. 3b is a sectional view of the needle module 4 along line b-b of FIG. 3a. It can be seen that the relative positions of the needle hub 11, the needle shield 20, and the needle housing 16 in this configuration of the needle module 4 allows for a radially inwards deflection of the arms 24 in response to a user pressing e.g. a thumb and a forefinger through the respective openings 19, following removal of the outer cap 10.

Figure 4:
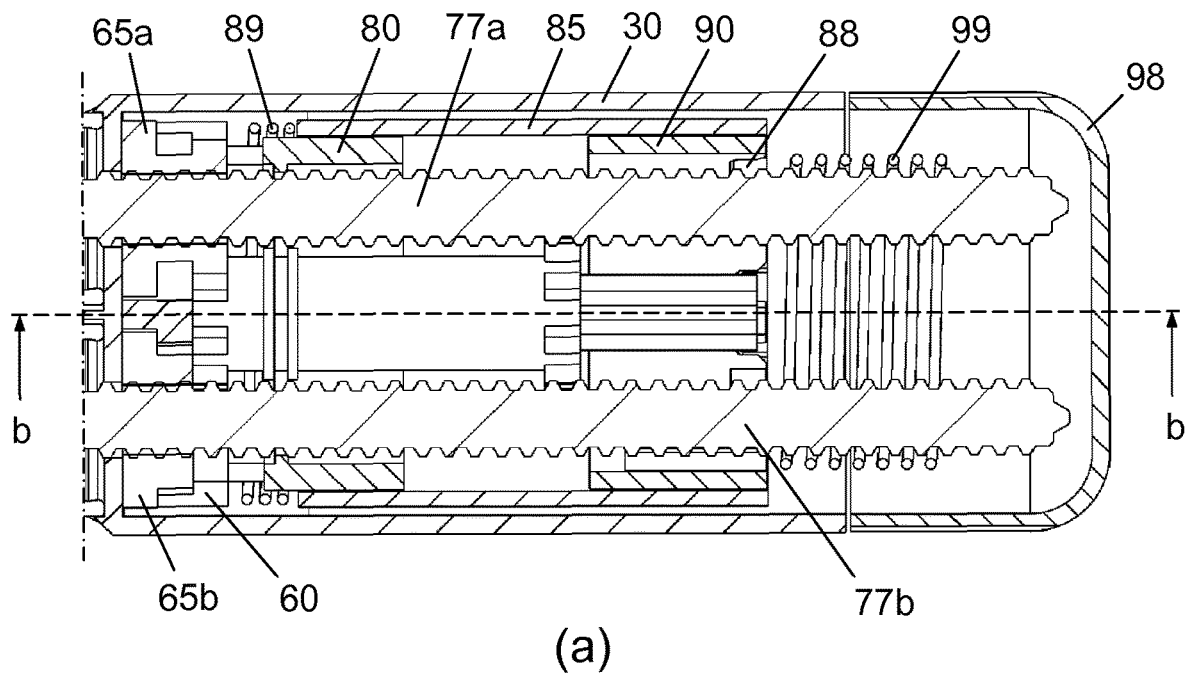
FIG. 4 shows two close-up sectional views of a proximal portion of the drug delivery device.
Figure 4:
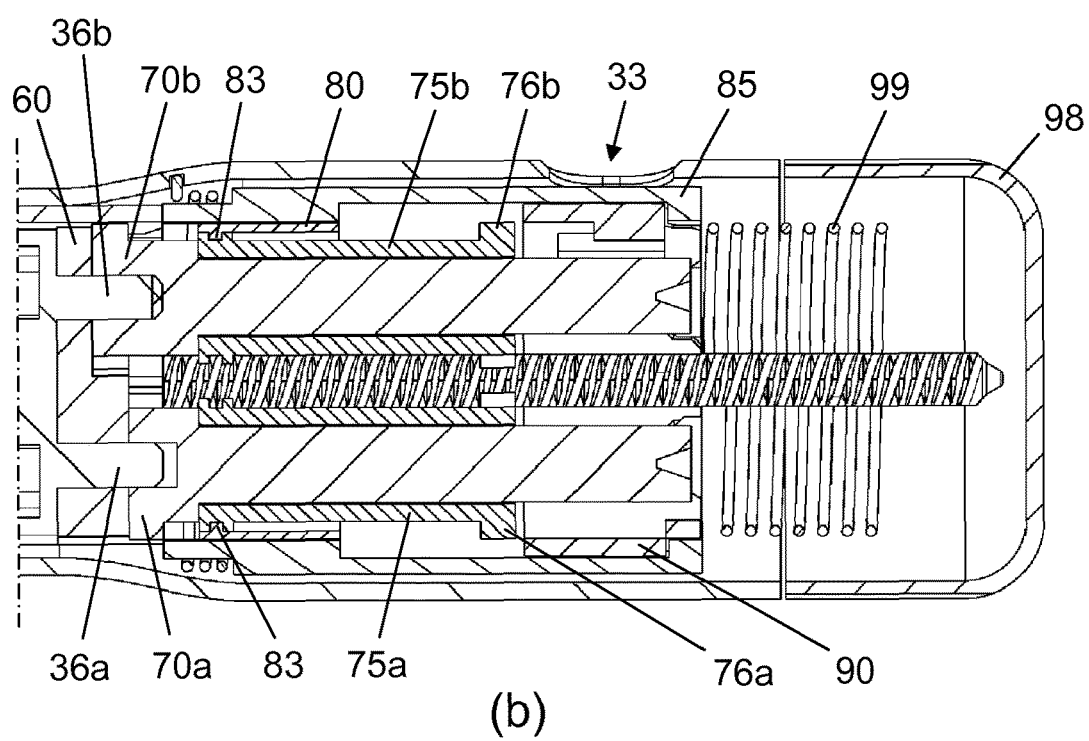

FIG. 4a is a close-up view of a proximal portion of the drug delivery device 2, 3 indicated by section Q in FIG. 2, displaying the various elements of the dose engine 3 in more detail. The drug delivery device 3 is in the dose setting state where a rotation of the dose dial 98 leads to a rotational positioning of the scale drum 90 in accordance with the desired dose size and a corresponding rotation of both the scale connector 85, due to the engagement between the radial protrusions 88 and the indents 92, and the dose locator 80, due to the presence of the splines 86 in the longitudinal tracks 82.

FIG. 4b is a sectional view of the proximal portion of the drug delivery device 2, 3 along line b-b of FIG. 4a. Notably, in this view a circular interior protrusion 83 on the dose locator 80 is visible, which interior protrusion 83 is used to axially fix the dose locator 80 to both the first top gear 75a and the second top gear 75b. Also, it can be seen that in the dose setting state of the drug delivery device 2, 3 the toothed rims 76a, 76b are disconnected from the scale drum 90.

Figure 5:
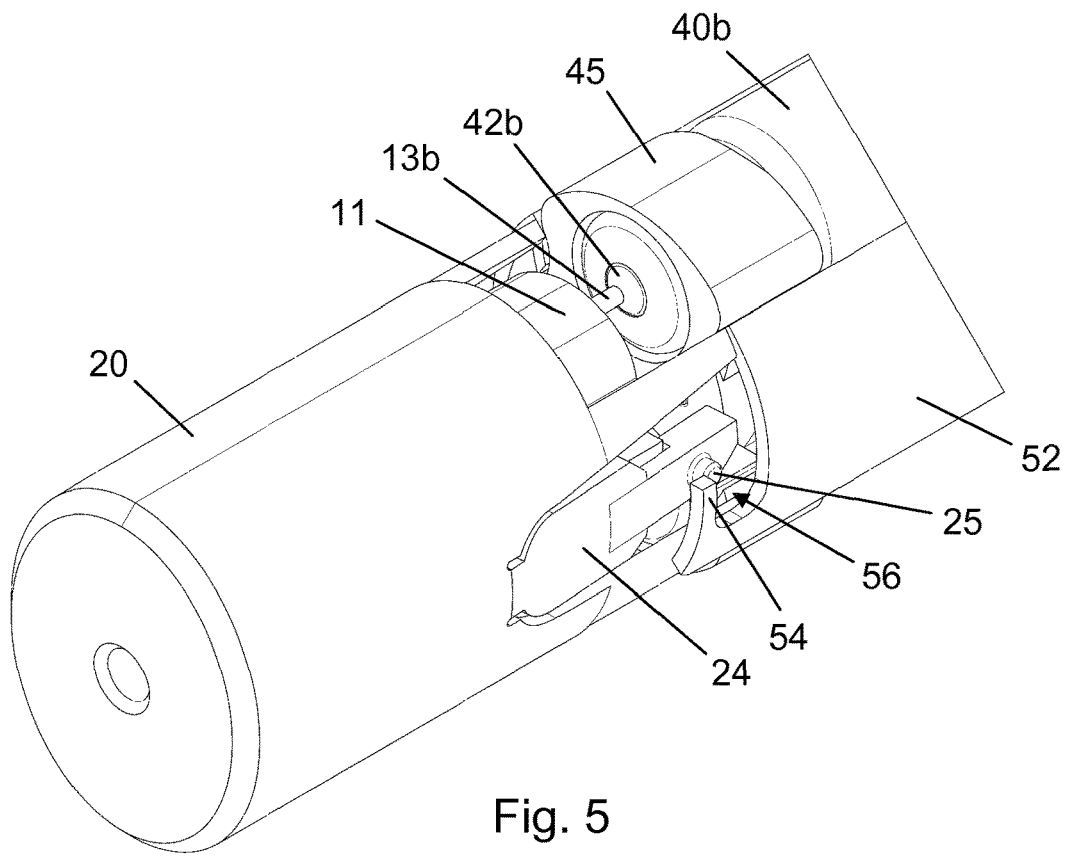
FIGS. 5 and 6 show a perspective view of parts of the needle module during mounting, respectively after mounting, of the needle module onto the drug delivery device.
Figure 6:
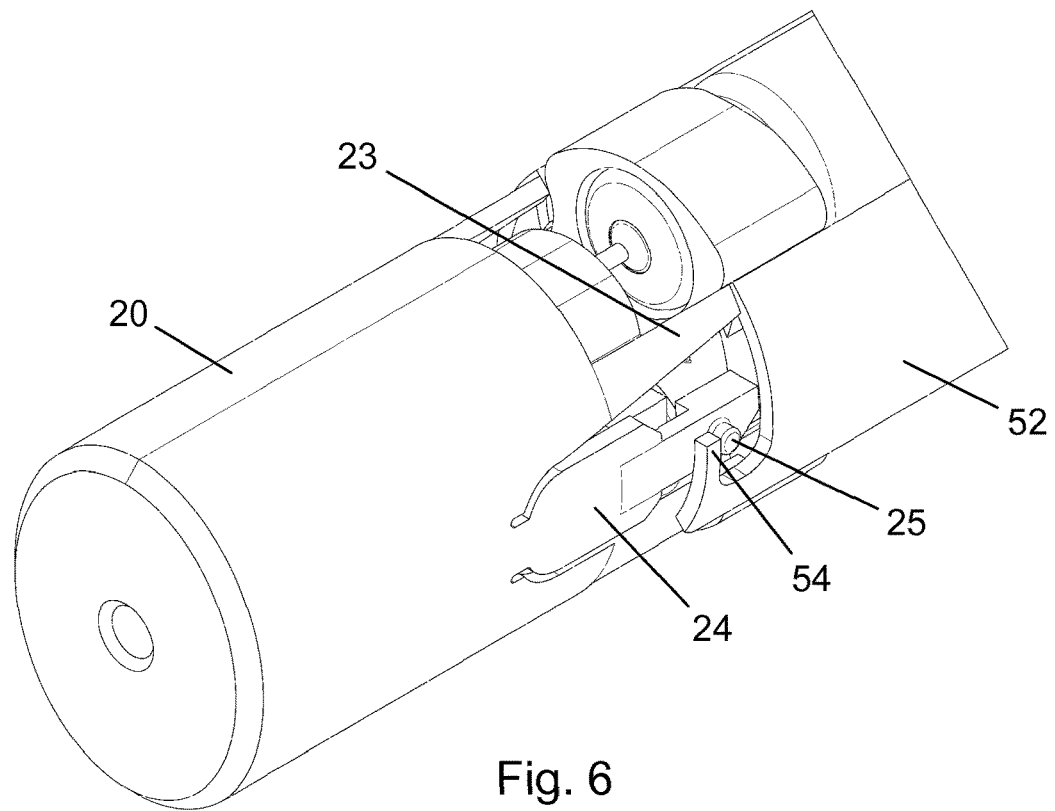

FIG. 5 is a perspective view of parts of the needle module 4 during attachment to the drug delivery device 2, 3. For the sake of clarity the needle housing 16 and the outer cap 10 have been omitted. The figure specifically shows how one of the arms 24 deflect radially inwardly, either prompted automatically during the converging relative axial motion between the needle shield 20 and the main body 30 by the interaction between dedicated geometries or caused by the user's compression through the opening 19, to allow the guide pin 25 to pass the retaining hook 54 and snap into the receiving space 56. In FIG. 6 the guide pin 25 is securely positioned in the receiving space 56 and the leg 23 abuts the second shield transfer element 52. On the opposite side of the needle hub 11 a similar connection has taken place between the other guide pin 25 and the first shield transfer element 51. Thereby, the needle shield 20 has become axially locked to the shield transfer elements 51, 52. Notably, in this attached state of the needle module 4 the back needles 13a, 13b have not yet penetrated the septa 42a, 42b, and the needle module 4 may therefore be removed from the drug delivery device 2, 3 simply by the user applying a compressive force through the openings 19 to depress the arms 24 and subsequently pulling the needle shield 20 axially away from the main body 30.

Figure 7:
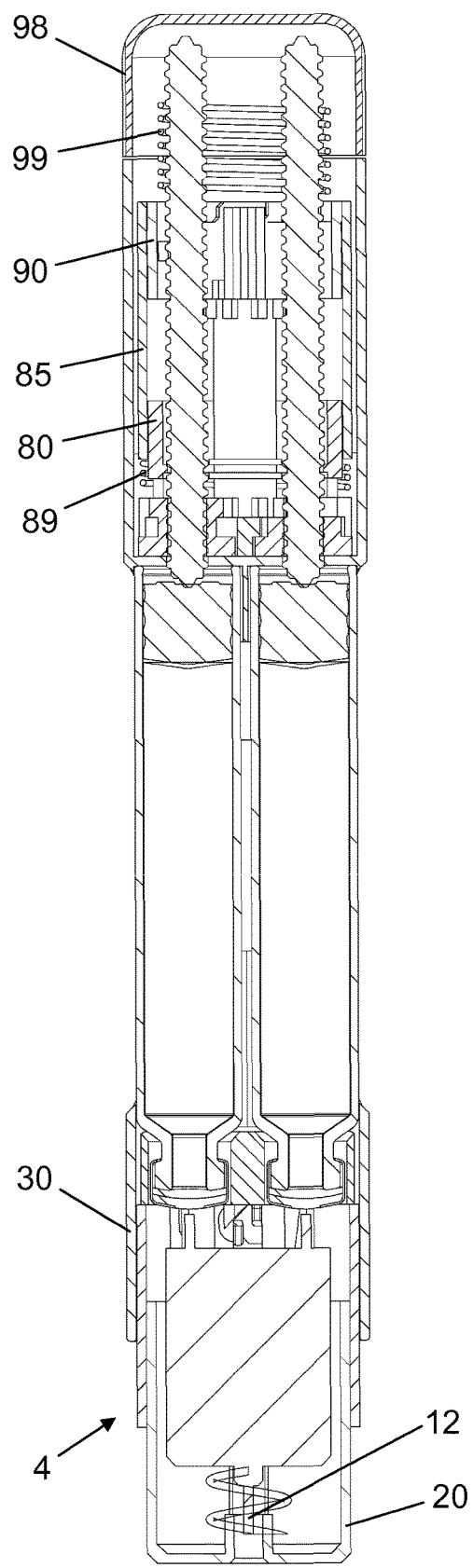
FIGS. 7-10 show longitudinal section views of the drug delivery system in various states during expelling of a dose of drug.

FIG. 7 is a longitudinal section view of the drug delivery system 1 in the attached state of the needle module 4, corresponding to FIG. 6, with the outer cap 10 removed. At this point a desired dose to be delivered is set by rotation of the dose dial 98. The rotation of the dose dial 98 results in an angular positioning of the scale drum 90 relative to the main body 30 as well as a torsional straining of the power spring 99. The power spring 99 is maintained in the strained state by a releasable ratchet mechanism (not shown). The dose ciphers 91 are successively viewable through the dose window 33 as the scale drum 90 is turned, and each offered dose size is associated with a unique angular position of the scale drum 90. Due to the rotational relationship between the scale drum 90 and the scale connector 85 and between the scale connector 85 and the dose locator 80, both the scale connector 85 and the dose locator 80 are angularly displaced relative to the main body 30 corresponding to the angular displacement of the scale drum 90, and the dose locator return spring 89, being arranged to act between the scale connector 85 and the main body 30, is torsionally strained, thereby providing a biasing torque to the scale connector 85 and the dose locator 80. The dose locator return spring 89 is maintained in the strained state by a releasable ratchet mechanism (not shown).

When a desired dose is set the drug delivery system 1 is ready to deliver a certain volume of the first substance followed by a certain volume of the second substance by release of the power spring 99. The particular volumes delivered are dictated by the chosen dose in accordance with the specific construction of the drug delivery device 2, 3.

Figure 8:
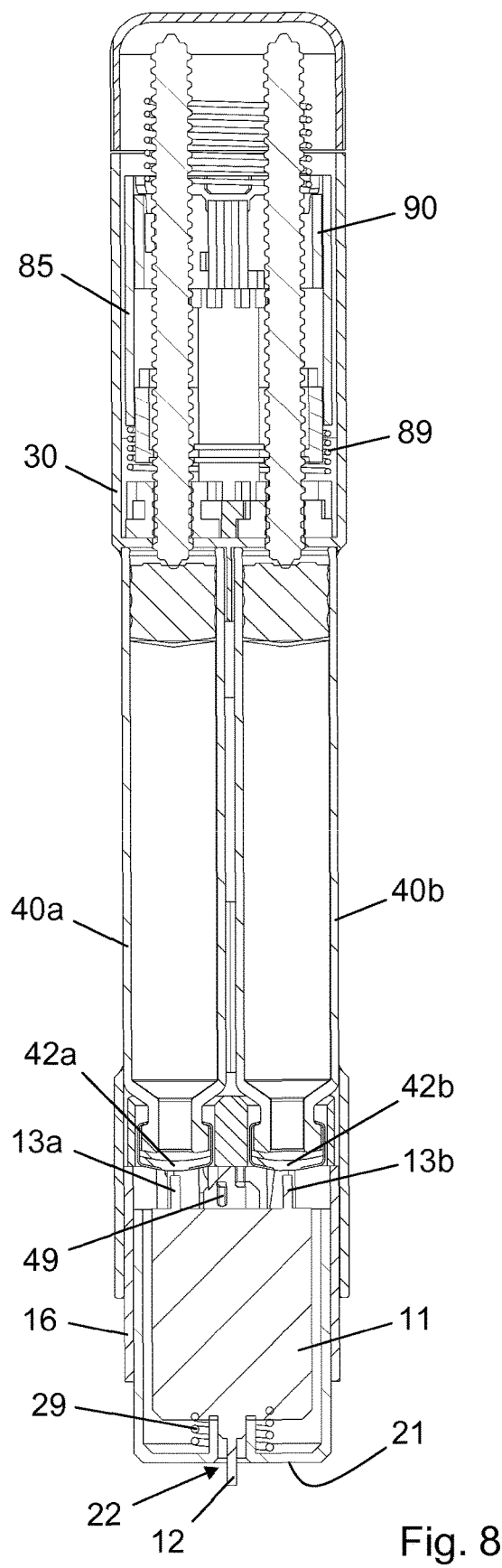

To administer the set dose the user places the end wall 21 on the skin at a desired injection site and presses the drug delivery system 1 against the skin. The chassis spring 49 is stiffer than the needle return spring 29, so firstly the needle return spring 29 will be compressed as the needle shield 20 slides on the outside of the needle hub 11, leading to a protrusion of the front needle 12 from the bore 22 and thereby an insertion of the front needle 12 into the skin. This is depicted in FIG. 8.

As the needle shield 20 moves proximally relative to the main body 30 the shield transfer elements 51, 52 move, accordingly, proximally relative to the bulkhead 31, whereby the abutment surface 55 applies a pushing force to the abutment surface 87, axially displacing the scale connector 85 and lifting the radial protrusions 88 out of engagement with the indents 92. The scale connector 85 is thereby rotationally disengaged from the scale drum 90. The proximal displacement of the scale connector 85 leads to a stretching of the dose locator return spring 89. The dose locator return spring 89 thus biases the scale connector 85, and thereby the shield transfer elements 51, 52 and the needle shield 20, distally relative to the main body 30.

Figure 9:
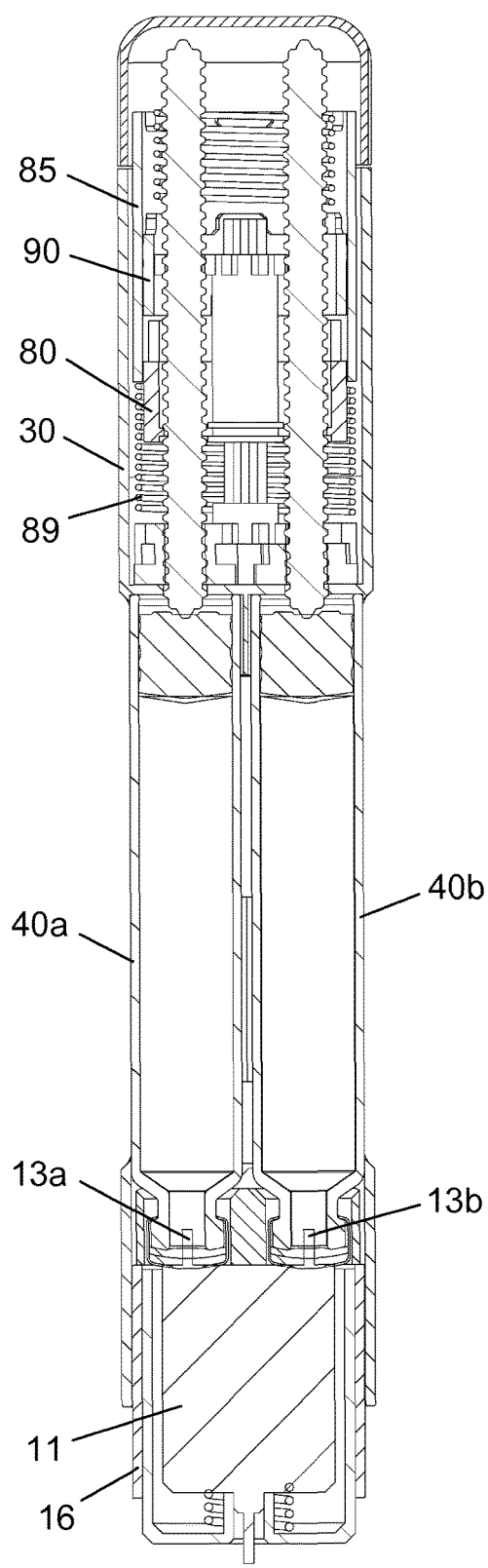

Subsequent to the above mentioned the pressing of the drug delivery system 1 against the skin will lead to a compression of the chassis spring 49 and a simultaneous penetration of the first septum 42a by the first back needle 13a and of the second septum 42b by the second back needle 13b as the needle hub 11 slides within the main body 30 in unison with the needle shield 20. This is depicted in FIG. 9. Fluid communication is thereby established between the first back needle 13a and the interior of the first cartridge 40a and between the second back needle 13b and the interior of the second cartridge 40b, and the needle module 4 is now in a connected state.

The additional proximal movement of the needle shield 20 leads to a further proximal movement of the shield transfer elements 51, 52, which causes the transfer leg 53 to enter into a dose specific pocket 81 and the abutment surface 55, resultantly, to axially displace the dose locator 80 relative to the main body 30. Since the abutment surface 55 still abuts the abutment surface 87 of one of the splines 86 the scale connector 85 is displaced a corresponding distance in the main body 30, further straining the dose locator return spring 89 axially.

Due to the axial fixation of the top gears 75a, 75b to the dose locator 80 via the interior protrusion 83 the aforementioned displacement of the dose locator 80 brings the toothed rims 76a, 76b into engagement with the teeth 94 on the scale drum 90. As the scale connector 85 reaches a specific point the power spring 99 is released, and the scale drum 90 is urged to rotate back to its initial angular position in the main body 30, thereby successively activating the first lay shaft 70a and the second lay shaft 70b, leading to a sequential administration of the first substance and the second substance. The dose specific positioning of the toothed rims 76a, 76b within the annular space defined by the scale drum 90 as well as the dose administration resulting from the return of the scale drum 90 are described further below in connection with FIGS. 11-19.

Figure 10:
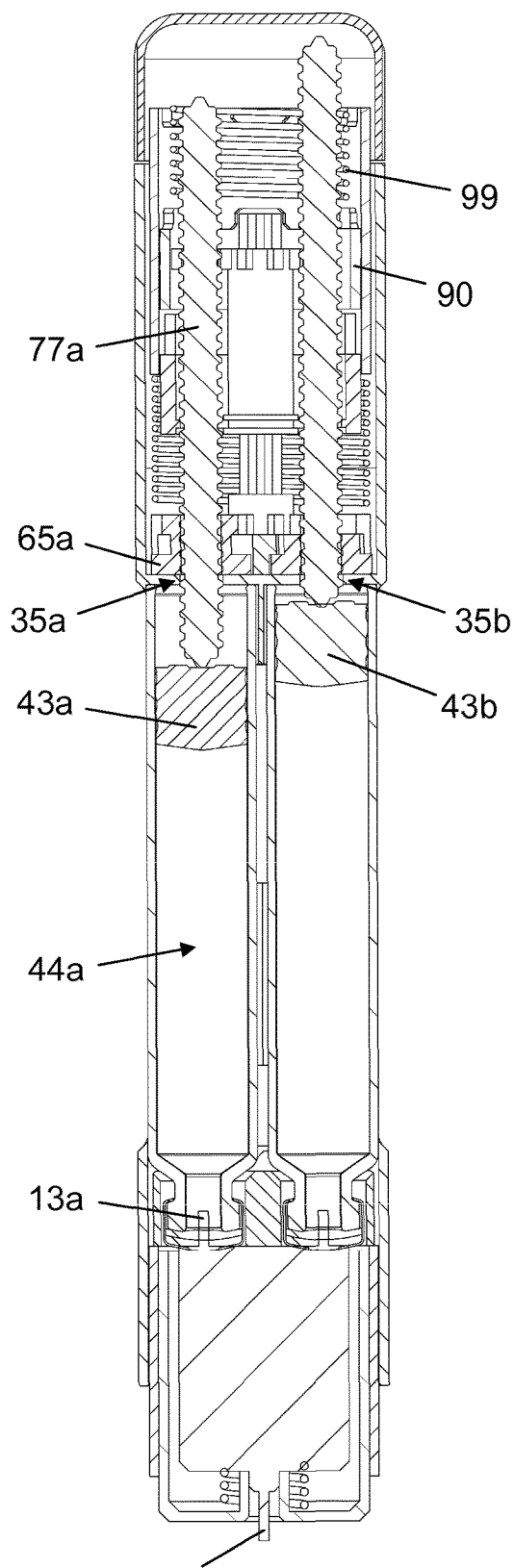

FIG. 10 shows the drug delivery system 1 in a state where the scale drum 90 has travelled exactly half of the angular distance towards its initial position. It is seen that only the first piston rod guide 65a has been activated at this point, leading to an advancement of the first piston rod 77a through the first through hole 35a, and that the second piston rod 77b has remained motionless relative to the second through hole 35b. Accordingly, the first piston 43a has been displaced in the first cartridge 40a and expelled the dose of the first substance from the first chamber 44a through the first back needle 13a and the front needle 12, while the second piston 43b is still in the full cartridge position. As the power spring 99 continues to lead the scale drum 90 back the first piston rod 77a will become motionless while the second piston rod 77b will be activated as a consequence of the second piston rod guide 65b being rotated. The delivery sequence will be clear from the below description.

In the present embodiment the drug delivery device 2, 3 offers five different doses, "dose 1"-"dose 5". As mentioned previously the dose is selected by the user by rotating the dose dial 98, and the rotation of the dose dial 98 leads to corresponding rotations of the scale drum 90 and the dose locator 80. The angular position of the dose locator in the main body 30 is therefore uniquely coupled to the selected dose.

FIGS. 11-14 sketch the dose delivery mechanism in four different stages, in combined perspective and sectional views, during delivery of "dose 3". For the sake of clarity elements such as the main body 30, the scale connector 85, and the dose locator return spring 89 are omitted from the views. Further, to enhance the visibility of the components within the annular space defined by the scale drum 90 the proximal half of the scale drum 90 has been cut away in the perspective views.

Figure 11:
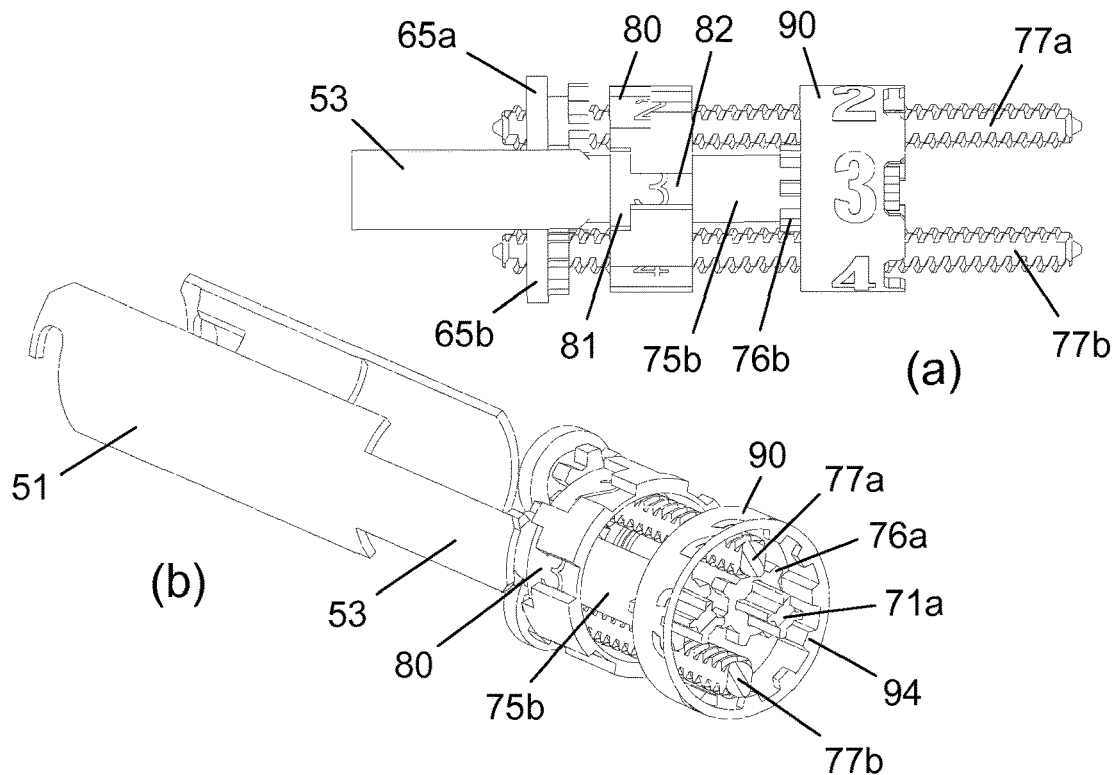
FIGS. 11-14 show different views of a dosing mechanism in the drug delivery device during one sequential substance administration.

FIG. 11 shows that following the setting of "dose 3" the scale drum 90 and the dose locator 80 are angularly aligned at "3". The proximal displacement of the first shield transfer element 51, and thereby of the transfer leg 53, relative to the main body 30 is predetermined and independent of the set dose. The shield transfer elements 51, 52 are axially locked to the needle shield 20 which is displaced the same distance proximally relative to the main body 30 every time the front needle 12 is positioned in the skin and the back needles 13a, 13b are pushed through the septa 42a, 42b. Hence, the transfer leg 53 is always displaced the same distance in response to the front needle 12 and the back needles 13a, 13b being inserted, regardless of the selected dose. However, the angular position of the dose locator 80 varies, and the respective depths of the pockets 81 correspond to respective doses such that the abutment surface 55 will interact with a pocket wall at varying axial positions, depending on the selected dose. This means that for five possible doses the dose locator 80 is displaced five different distances axially in response to the front needle 12 and the back needles 13a, 13b being inserted, and that the actual displacement of the dose locator 80 is specific to a particular dose.

The view in FIG. 11 corresponds to the attached state of the needle module 4 shown in FIG. 7, where the back needles 13a, 13b have not yet penetrated the septa 42a, 42b. It is seen that the transfer leg 53 has not yet entered into the specific pocket 81 pertaining to "dose 3" and that the toothed rims 76a, 76b are out of engagement with the teeth 94.

Figure 12:
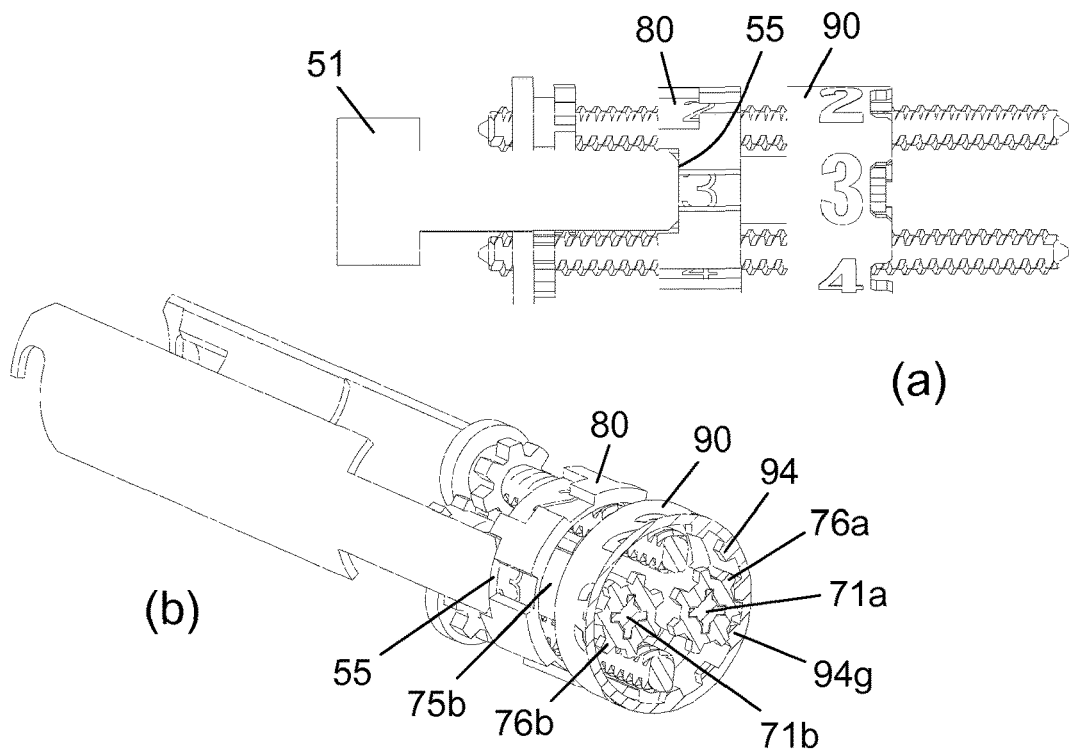

The view in FIG. 12 corresponds to the connected state of the needle module 4 shown in FIG. 9. At this point the transfer leg 53 has entered into the pocket 81 and the abutment surface 55 has forced the dose locator 80 to displace axially towards the scale drum 90 a particular distance dictated by the depth of the pocket 81. As the dose locator 80 moves axially the top gears 75a, 75b slide correspondingly along the cruciform shaft portions 71a, 71b of the respective lay shafts 70a, 70b, and the axial displacement of the toothed rims 76a, 76b is accordingly strictly correlated with the selected dose. The teeth 94 on the interior surface of the scale drum 90 are distributed in five different axial layers corresponding to the five selectable doses, "dose 1"-"dose 5", and the toothed rims 76a, 76b will interact differently with the teeth 94 in the five different axial layers, as described below in connection with FIGS. 15-19.

FIG. 12b shows how the axial displacement of the dose locator 80 has caused the toothed rims 76a, 76b to become positioned within the scale drum 90 at the "dose 3" layer of teeth 94 in which a first meshing tooth 94g is ready to engage with the toothed rim 76a and consequently rotate the first top gear 75a.

Figure 13:
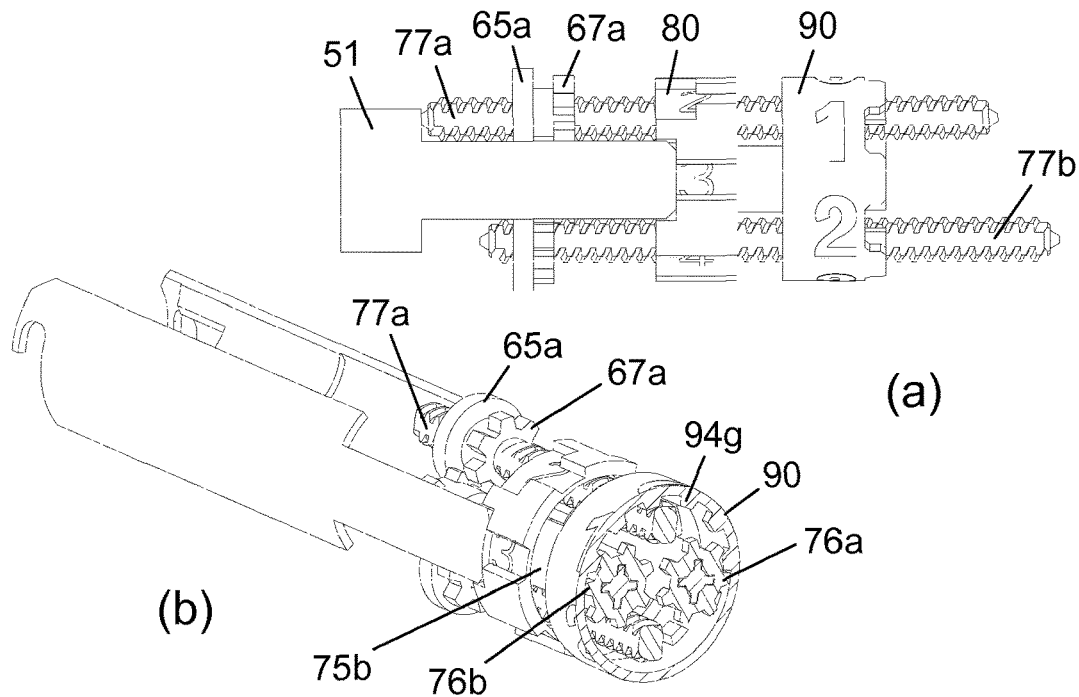

The view in FIG. 13 corresponds to the half-completed dose view of FIG. 10. The scale drum 90 has been rotated by the torsionally relaxing power spring 99 and has undergone exactly half of the angular displacement from its dose setting position. This has caused the first meshing tooth 94g and two immediately succeeding teeth to rotate the first top gear 75a which due to the rotational engagement between the toothed head 72a and the toothed rim 67a in turn has rotated the first piston rod guide 65a. The threaded interface between the pass-through 66a and the first piston rod 77a and the splined connection of the first piston rod 77a to the bulkhead 31 has consequently caused the first piston rod 77a to advance axially a dose specific distance. This is best seen in FIG. 13a.

The teeth 94 are now in a position where further rotation of the scale drum 90 will cause interaction with the toothed rim 76b and thereby rotation of the second top gear 75b. This can be seen from FIG. 13b. Notably, since the scale drum 90 and the scale connector 85 are rotationally decoupled and since the dose locator 80 is rotationally locked to the transfer leg 53, the scale drum 90 rotates relative to the dose locator 80 during this part of the dose administration.

Figure 14:
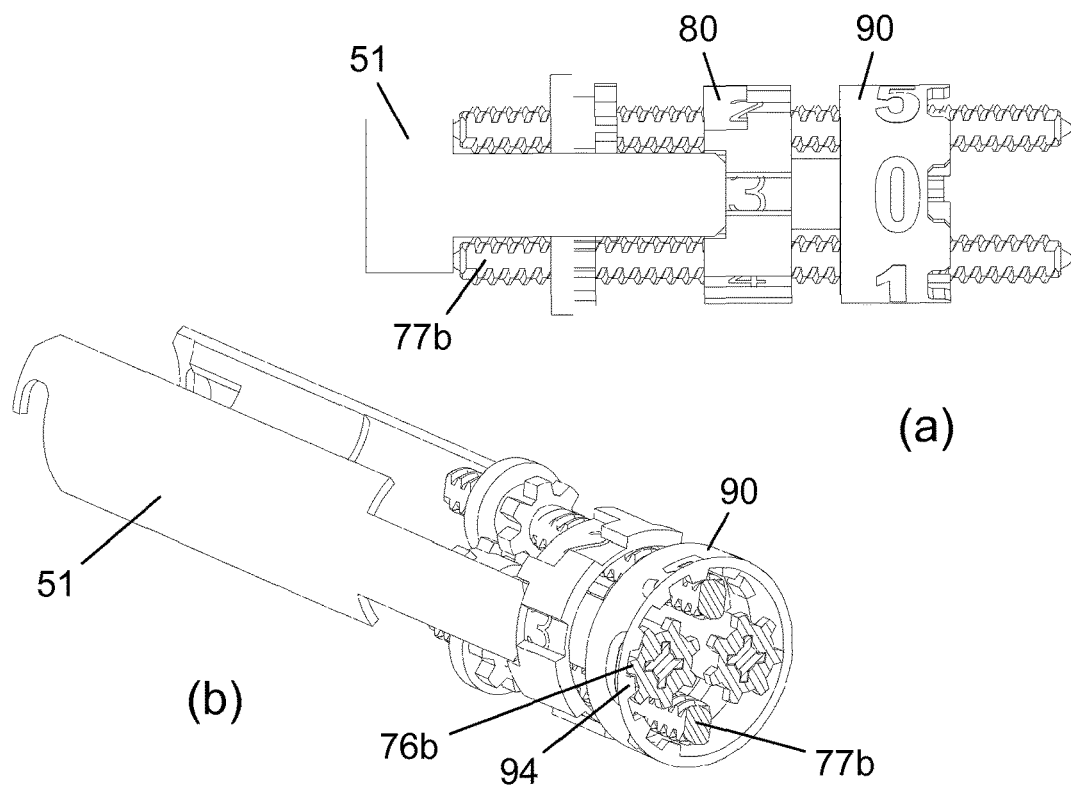

In FIG. 14 the scale drum 90 has undergone the second half of the rotation back to its initial position which has caused an axial advancement of the second piston rod 77b in response to three teeth 94 having consecutively meshed with the toothed rim 76b. The advancement of the second piston rod 77b is best seen in FIG. 14a, while FIG. 14b best illustrates the movement of the three teeth 94 in question, when compared to FIG. 13b.

So, while the dose setting action serves to angularly position the scale drum 90 relative to the main body 30, the needle module connecting action serves to, apart from establish a required flow path from the cartridges 40a, 40b to the body, axially position the top gears 75a, 75b relative to the angularly positioned scale drum 90. These two actions together ensure that a volume of the first substance and a volume of the second substance are administered sequentially in accordance with the set dose, as the power spring 99 subsequently releases a portion of its stored energy. It is noted that the respective administered volumes of the first substance and the second substance may be identical or may be different, depending on the specific construction of the drug delivery device 2, 3 chosen by the manufacturer. For example, the first interrupted thread 78a and the second interrupted thread 78b may have different pitches, whereby identical angular displacements of the first top gear 75a and the second top gear 75b will lead to different axial displacements of the first piston rod 77a and the second piston rod 77b and thereby of the first piston 43a and the second piston 43b.

FIGS. 15-19 show top views of the scale drum 90, the first top gear 75a, the second top gear 75b, the first piston rod 77a, and the second piston rod 77b in five different cross-sections of the scale drum 90, corresponding to the aforementioned five axial layers. For the sake of clarity, each cross-sectional view shows only the configuration of teeth 94 that are active in the corresponding axial layer. Each view shows the components in a state where a dose of the first substance has been administered from the drug delivery system 1 and where an administration of a dose of the second substance is about to commence.

Figure 15:
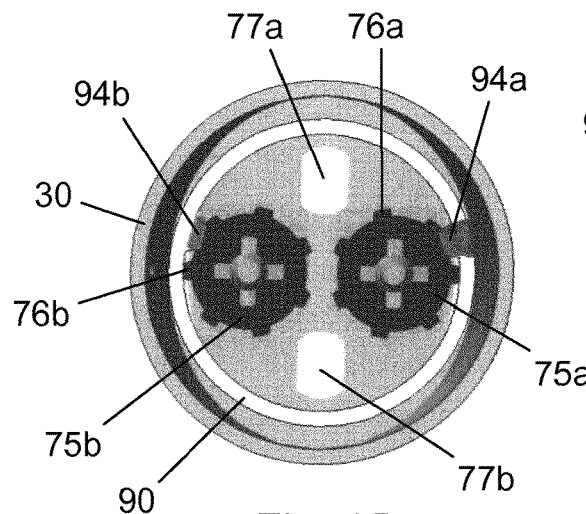
FIGS. 15-19 show cross-sectional top views of the drive structure engagement for five different dose sizes.

FIG. 15 is a cross-sectional view through the "dose 1" layer of the scale drum 90. For the present embodiment of the invention the toothed rims 76a, 76b reach this layer by the shortest axial travel of the dose locator 80 caused by the displacement of the transfer leg 53, since by the angular positioning of the dose locator 80 corresponding to a set dose of size "dose 1" the transfer leg 53 becomes aligned with the deepest of the pockets 81. As can be seen from the figure two teeth 94a, 94b are present in this layer. The teeth 94a, 94b are arranged such that when a dose of size "dose 1" is set and the needle module 4 is in the connected state the tooth 94a will be positioned adjacent to, and ready to engage with, a tooth on the toothed rim 76a of the first top gear 75a, while the tooth 94b will be positioned a short distance away from the toothed rim 76b of the second top gear 75b.

As the scale drum 90 rotates back to its initial, "0", position in response to the release of the power spring 99 first the tooth 94a engages with the toothed rim 76a and rotates the first top gear 75a while the tooth 94b approaches the toothed rim 76b, then the tooth 94a disengages from the toothed rim 76a just as the tooth 94b reaches the toothed rim 76b. This is the state shown in FIG. 15. At this point the first top gear 75a has been rotated "x" degrees leading to a corresponding rotation of the first piston rod guide 65a due to the rotational interlocked relationship between the first top gear 75a and the first lay shaft 70a and the rotational engagement between the toothed head 72a and the toothed rim 67a. The rotation of the first piston rod guide 65a by "x" degrees has led to a distal displacement of the first piston rod 77a, and thereby of the first piston 43a, the magnitude of the displacement being determined by the pitch of the threaded connection between the interrupted thread 78a and the pass-through 66a. Consequently, a volume of the first substance has been expelled from the first chamber 44a through the first back needle 13a and the front needle 12.

The continued rotation of the scale drum 90 now leads the tooth 94b to engage with the toothed rim 76b and rotate the second top gear 75b "x" degrees, while the tooth 94a moves freely along a part-circular path. Thereby, the second piston rod 77b is activated to expel a dose of the second substance from the second chamber 44b through the second back needle 13b and the front needle 12, similarly to the above described expelling of the first substance, while the first piston rod 77a remains stationary. A true sequential administration of the first substance and the second substance is thus realised in response to an angular displacement of the scale drum 90. Notably, the angular displacement of the scale drum 90 needed to administer "dose 1" is less than 360°.

Figure 16:
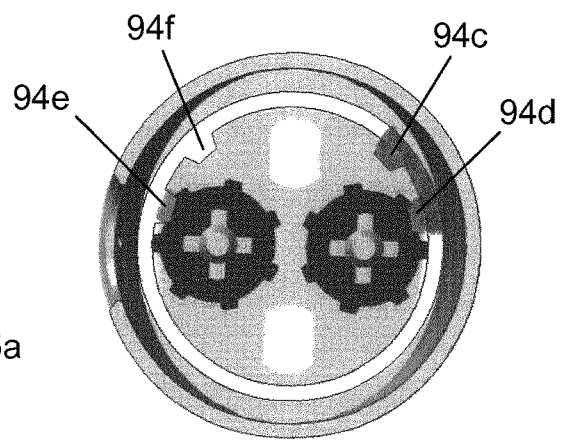

FIG. 16 is a cross-sectional view through the "dose 2" layer of the scale drum 90. In this layer four teeth 94c, 94d, 94e, 94f are distributed along the inner circumference of the scale drum 90. The teeth 94c, 94d are dedicated to interact with the toothed rim 76a of the first top gear 75a, while the teeth 94e, 94f are dedicated to interact with the toothed rim 76b of the second top gear 75b. In this case the teeth 94c, 94d have both engaged with and disengaged from the toothed rim 76a before the teeth 94e, 94f move into engagement with the toothed rim 76b, thereby securing the sequential administration. Since two teeth 94 interact with each toothed rim 76a, 76b the respective top gears 75a, 75b are rotated more during administration of "dose 2" than during administration of "dose 1", and the respective piston rods 77a, 77b are accordingly advanced a longer distance distally to expel a larger volume of the first substance, respectively the second substance.

Figure 17:
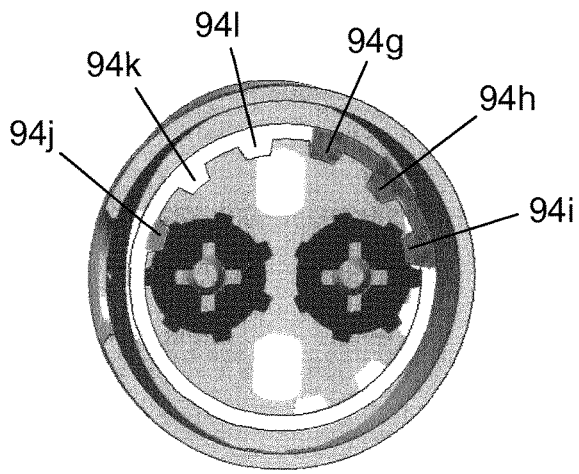

FIG. 17 is a cross-sectional view through the "dose 3" layer of the scale drum 90. This is the layer shown in FIGS. 11-14. In this layer six teeth 94g, 94h, 94i, 94j, 94k, 94l are distributed along the inner circumference of the scale drum 90. Three of the teeth 94g, 94h, 94i are dedicated to interact with the toothed rim 76a of the first top gear 75a, and the other three teeth 94j, 94k, 94l are dedicated to interact with the toothed rim 76b of the second top gear 75b. The state shown in FIG. 17 corresponds to the state shown in FIG. 13b. The first meshing tooth 94g has firstly interacted with the toothed rim 76a, followed by the teeth 94h, 94i. As the tooth 94i disengages from the toothed rim 76a the tooth 94j reaches the toothed rim 76b and the remaining rotation of the scale drum 90 causes the teeth 94j, 94k, 94l to consecutively engage with the toothed rim 76b and rotate the second top gear 75b.

Figure 18:
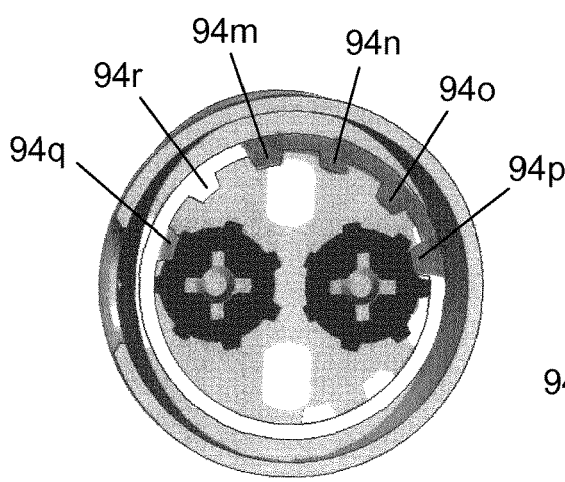

FIG. 18 is a cross-sectional view through the "dose 4" layer of the scale drum 90. This layer also has six active teeth 94m, 94n, 94o, 94p, 94q, 94r, but unlike the previous layers in this layer two teeth 94m, 94n are shared in the sense that they are used to both interact with the toothed rim 76a of the first top gear 75a and with the toothed rim 76b of the second top gear 75b. This way, four teeth 94m, 94n, 94o, 94p are used to rotate the first top gear 75a and four teeth 94q, 94r, 94m, 94n are used to rotate the second top gear 75b.

Figure 19:
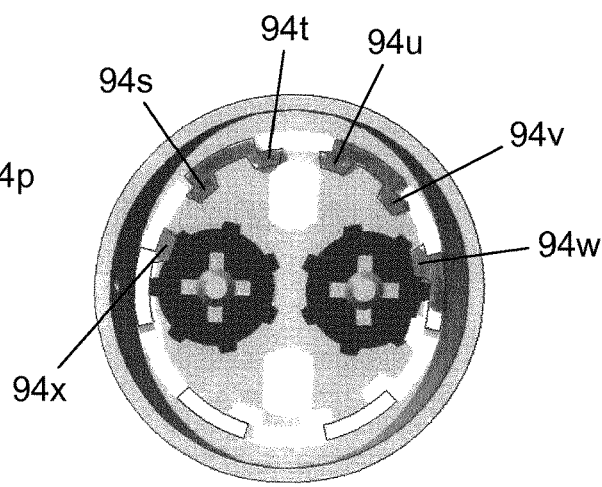

FIG. 19 is a cross-sectional view through the "dose 5" layer of the scale drum 90. Also in this layer six teeth 94s, 94t, 94u, 94v, 94w, 94x are present, but here four teeth 94s, 94t, 94u, 94v are shared such that five teeth 94s, 94t, 94u, 94v, 94w are used to rotate the first top gear 75a and five teeth 94t, 94u, 94v, 94w, 94x are used to rotate the second top gear 75b. Thereby, to administer "dose 5" the scale drum 90 performs almost one complete revolution with respect to the main body 30.

The particular arrangement of the teeth 94 in the various axial layers of the scale drum 90 ensure that once a last interacting tooth leaves the toothed rim 76a of the first top gear 75a a first interacting tooth is about to enter into engagement with the toothed rim 76b of the second top gear 75b. Thereby, a smooth transition between the administration of the first substance and the second substance is guaranteed in the sense that the scale drum 90 will not be able to rotate very long without a tooth being in engagement with one of the toothed rims 76a, 76b. If the teeth 94 were not arranged in this manner the scale drum 90 would be able to gain momentum during movement between interaction with the respective toothed rims 76a, 76b, induced by the torque applying power spring 99, and this could potentially lead to an impact with the toothed rim 76b of the second top gear 75b which would be unpleasant to the user.

Figure 20:
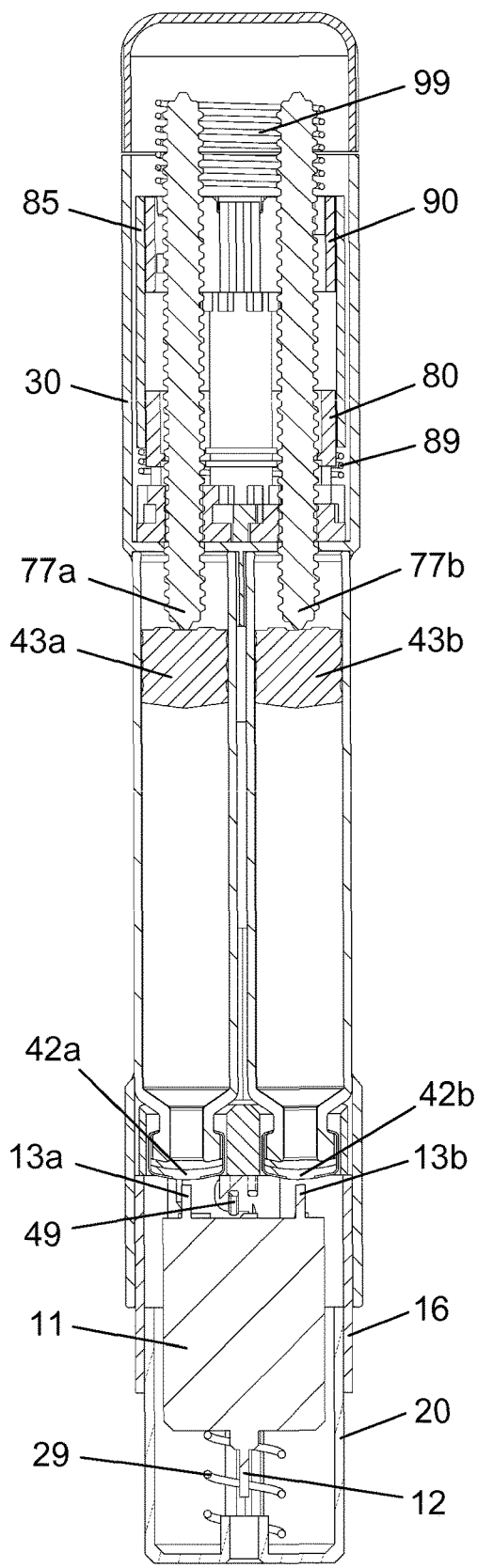
FIG. 20 is a longitudinal section view of the drug delivery system following a sequential dose administration.

FIG. 20 is a longitudinal section view of the drug delivery system 1 after completion of a dose administration and retraction of the front needle 12 from the skin. The first piston 43a and the second piston 43b have been displaced distally the same distance by the respective piston rods 77a, 77b, so the administered volume of the first substance and the administered volume of the second substance is the same.

During retraction of the front needle 12 from the skin because the chassis spring 49 is stiffer than the needle return spring 29 the back needles 13a, 13b are pulled out of the respective septa 42a, 42b before the front needle 12 actually leaves the body. This is important to minimise the risk of contaminating the remaining contents of the respective cartridges 40a, 40b. As the chassis spring 49 causes an axial motion of the needle hub 11 and the needle shield 20 relative to the main body 30 the shield transfer elements 51, 52 are displaced distally in the main body 30. The transfer leg 30 is thereby moved out of the pocket 81, allowing the dose locator return spring 89 to release and automatically rotate the dose locator 80 back to its initial angular position in the main body 30, the "0" dose alignment with the scale drum 90. Furthermore, the dose locator return spring 89 also returns the scale connector 85, and with that the dose locator 80, to their respective initial axial positions in the main body 30. The axial return movement of the dose locator 80 brings the toothed rims 76a, 76b out of the annular space defined by the scale drum 90 and thereby disengages the top gears 75a, 75b from the scale drum 90. The axial return movement of the scale connector 85 leads to a reengagement of the radial protrusions 88 with the indents 92, whereby the scale connector 85 is once again rotationally locked to the scale drum 90.

Figure 21:
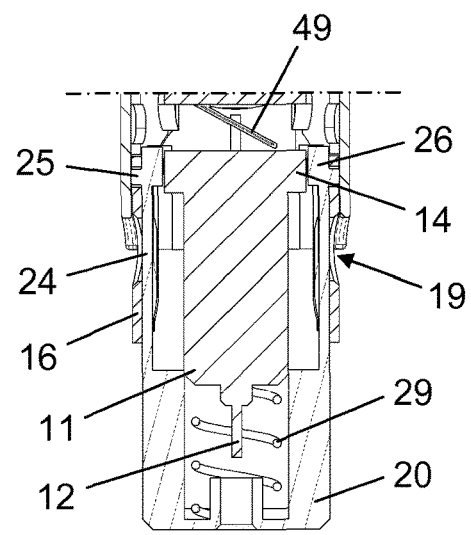
FIG. 21 is a longitudinal section view of the needle module in a locked out state.

FIG. 21 is a longitudinal section view of the needle module 4 in the state shown in FIG. 20. The section view corresponds to the section view shown in FIG. 3b. It can be seen that the needle shield 20 is further advanced by the needle return spring 29 in this state than in the pre-use state shown in FIG. 3b. This is obtained by use of a type of spring driven return mechanism commonly used in ball-pens to retract the marking point into the pen body. In the present case the extension of the needle shield 20 relative to the front needle 12 causes an alignment of the respective thickened portions 26 with the respective raised surfaces 14. This alignment prevents a radial deflection of the arms 24 by depression through the openings 19, thereby ensuring a radial immobilisation of the guide pins 25 which effectively prevents the needle module 4 from being reused, as will be clear from the following.

Figure 22:
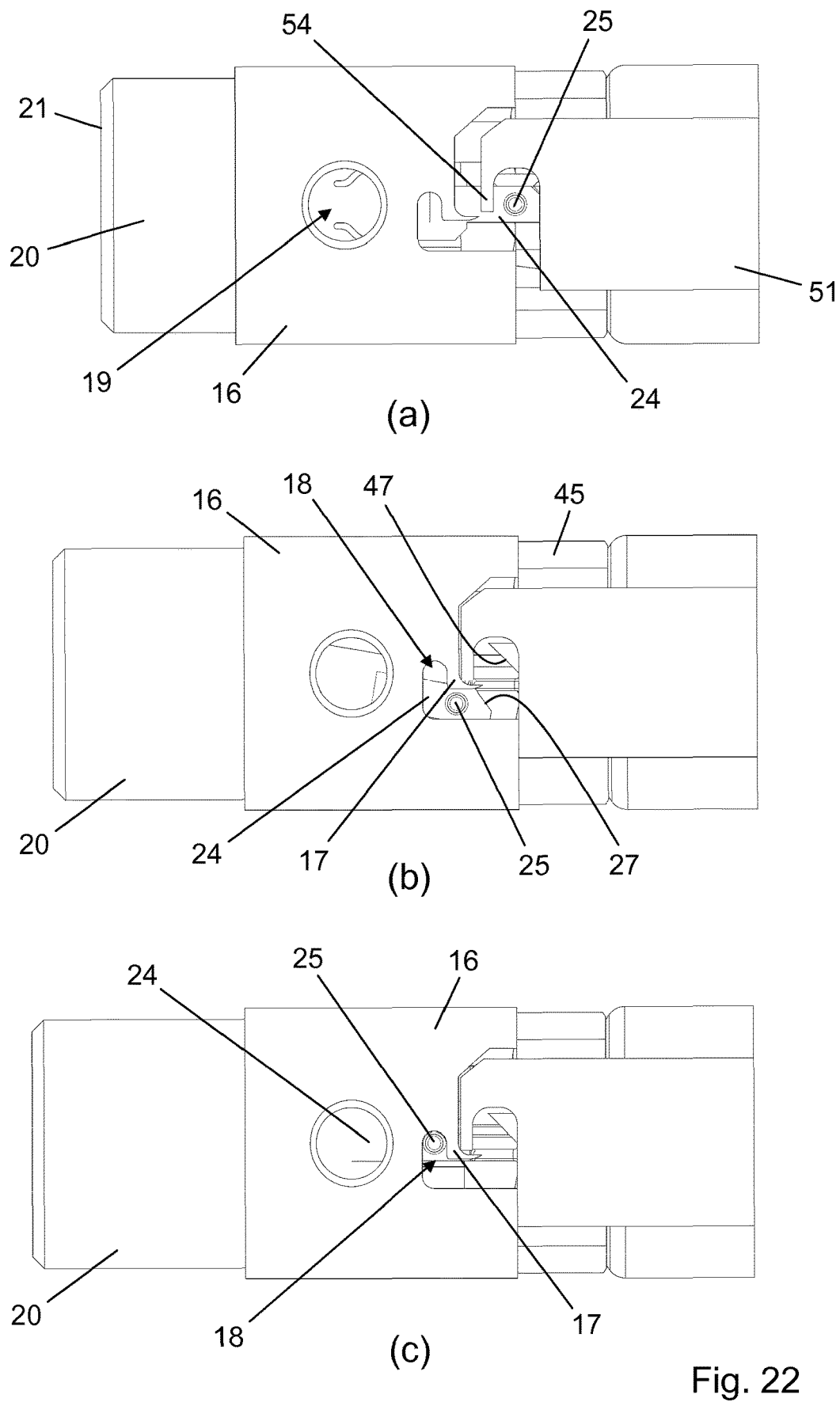
FIG. 22 shows the mechanism for locking out the needle module.

FIG. 22 illustrates the mechanism which prevents the needle module 4 from being used again after a completed dose administration. In FIG. 22a the guide pin 25 is positioned in the receiving space 56 behind the retaining hook 54. As the arm 24 begins to move axially relative to the first transfer shield 51 due to the needle return spring 29 advancing the needle shield 20 relative to the needle housing 16 the shield chamfer 27 slides along the chassis chamfer 47 and thereby causes a lateral deflection of the arm 24. This lateral deflection leads the guide pin 25 around the retaining hook 54 and the finger 17 and into the bayonet track 18, as seen in FIG. 22b.

As the axial movement of the needle shield 20 continues the guide pin 25 passes the finger 17 and the arm 24 pivots back to the non-deflected position, causing the guide pin 25 to move to the bottom of the bayonet track 18, as shown in FIG. 22c. The guide pin 25 is now securely positioned in the bayonet track 18 between the finger 17 and the main structure of the needle housing 16, and the needle shield 20 is thereby axially locked to the needle housing 16 in the extended position in which the front needle 12 is fully covered. Because the guide pin 25 is also radially immobilised, as described above, it is not possible for the user to expose the front needle 12 without damaging the needle module 4. A reuse of the needle module 4 is thereby prevented, which is important in order to reduce the risk of skin reactions as well as contamination and/or cross-contamination of the remaining contents of the cartridges 40a, 40b.

The invention claimed is:

1. A drug delivery system comprising:
    a drug delivery device carrying at least one reservoir, and
    a needle unit being attachable to the drug delivery device in axial extension thereof and adapted to establish a flow way between the at least one reservoir and a drug delivery site, the needle unit comprising:
        a needle structure comprising a front needle portion for entering the drug delivery site, and at least one back needle portion for insertion into the at least one reservoir, and
        a needle shield comprising a longitudinally extending arm,
    wherein
    the needle shield and the needle structure are capable of undergoing relative axial motion between an accommodating relative position in which the needle structure is completely accommodated within the needle shield, and a protruding relative position in which the front needle portion protrudes from the needle shield, the needle shield and the needle structure being biased towards the accommodating relative position by a first bias force,
    when the needle unit is attached to the drug delivery device the needle structure and the at least one reservoir are capable of undergoing relative axial motion between a disconnected relative position in which the at least one back needle portion is spaced apart from the at least one reservoir, and a connected relative position in which the at least one back needle portion and the at least one reservoir are fluidly connected, the needle structure and the at least one reservoir being biased towards the disconnected relative position by a second bias force,
    the second bias force is greater than the first bias force, such that when an axial compressive force presses the needle unit and the drug delivery device together the needle shield and the needle structure reach the protruding relative position before the needle structure and the at least one reservoir reach the connected relative position, and when the compressive force is discontinued the needle shield and the needle structure reach the accommodating relative position after the needle structure and the at least one reservoir reach the disconnected relative position,
    the needle unit further comprises a needle housing surrounding respective portions of the needle structure and the needle shield, the needle housing comprising a cylindrical wall having an opening therein, and
    wherein the opening is aligned with the longitudinally extending arm, allowing a user to apply a radial force to the longitudinally extending arm through the opening.

2. The drug delivery system according to claim 1, wherein the first bias force is provided by a first spring member arranged to act between the needle shield and a distally directed surface of the needle structure, and the second bias force is provided by a second spring member arranged on a distal end surface of the drug delivery device.

3. The drug delivery system according to claim 1, wherein the at least one reservoir comprises a first cartridge having a first penetrable septum and a second cartridge having a second penetrable septum, and the at least one back needle portion comprises a first back needle portion and a second back needle portion, each of the first back needle portion and the second back needle portion being fluidly connected with the front needle portion, and
    wherein the first back needle portion is adapted to penetrate the first penetrable septum to establish a first flow way between the first cartridge and the front needle portion, and the second back needle portion is adapted to penetrate the second penetrable septum to establish a second flow way between the second cartridge and the front needle portion.

4. The drug delivery system according to claim 1, wherein the longitudinally extending arm carries a protrusion, and the drug delivery device comprises a retaining hook adapted to interact with the protrusion to secure the needle unit on the drug delivery device,
    wherein in a pre-connected state of the needle structure the longitudinally extending arm is radially deflectable relative to a remaining portion of the needle shield from a non-deflected position in which the retaining hook is capable of interacting with the protrusion to a radially deflected position in which the retaining hook is incapable of interacting with the protrusion, and
    wherein the longitudinally extending arm is biased towards the non-deflected position.

5. The drug delivery system according to claim 4, wherein the longitudinally extending arm is further laterally deflectable relative to the remaining portion of the needle shield from the non-deflected position to a laterally deflected position against a lateral bias force biasing the longitudinally extending arm towards the non-deflected position, wherein the needle housing further comprises a bayonet track adapted to receive and retain the protrusion, wherein the longitudinally extending arm comprises a first ramp surface and the drug delivery device comprises a second ramp surface, the first ramp surface and the second ramp surface being arranged to slide along one another during relative axial motion of the needle structure and the at least one reservoir from the connected relative position to the disconnected relative position, thereby causing the longitudinally extending arm to move from the non-deflected position to the laterally deflected position and back to the non-deflected position, guiding the protrusion from the retaining hook to an end portion of the bayonet track, wherein the needle shield and the needle structure are configured to undergo a final relative axial motion from the accommodating relative position to a post-use accommodating relative position in response to the relative axial motion of the needle structure and the at least one reservoir from the connected relative position to the disconnected relative position, and wherein the needle structure further comprises a radial protuberance which is moved into radial alignment with the protrusion during the final relative axial motion between the needle shield and the needle structure.

* * * * *